US012551409B2

(12) United States Patent
Marangoz et al.

(10) Patent No.: US 12,551,409 B2
(45) Date of Patent: Feb. 17, 2026

(54) PROCESS FOR MANUFACTURING A COMPRESSED PRODUCT

(71) Applicant: Perfetti Van Melle S.P.A., Lainate (IT)

(72) Inventors: Güven Marangoz, KT Sittard (NL); Joaquin Antonio Lizano Iglesias, KT Sittard (NL); Alessandro Bottini, Lainate (IT)

(73) Assignee: Perfetti Van Melle S.P.A., Lainate (IT)

( * ) Notice: Subject to any disclaimer, the term of this patent is extended or adjusted under 35 U.S.C. 154(b) by 602 days.

(21) Appl. No.: 17/999,925

(22) PCT Filed: May 25, 2021

(86) PCT No.: PCT/IB2021/054502
§ 371 (c)(1),
(2) Date: Nov. 27, 2022

(87) PCT Pub. No.: WO2021/240348
PCT Pub. Date: Dec. 2, 2021

(65) Prior Publication Data

US 2023/0233410 A1 Jul. 27, 2023

(30) Foreign Application Priority Data

May 28, 2020 (IT) ........................ 102020000012685

(51) Int. Cl.

| | |
|---|---|
| ***A61J 3/10*** | (2006.01) |
| ***A61K 9/20*** | (2006.01) |
| ***B30B 11/08*** | (2006.01) |
| ***B30B 11/34*** | (2006.01) |

(52) U.S. Cl.
CPC ............... *A61J 3/10* (2013.01); *A61K 9/2095* (2013.01); *B30B 11/08* (2013.01); *B30B 11/34* (2013.01)

(58) Field of Classification Search
CPC .......... A61J 3/10; A61K 9/2095; B30B 11/08; B30B 11/34
See application file for complete search history.

(56) References Cited

U.S. PATENT DOCUMENTS

| | | | | |
|---|---|---|---|---|
| 2003/0068367 | A1 | 4/2003 | Sowden et al. | |
| 2011/0068511 | A1 | 3/2011 | Sowden et al. | |
| 2017/0197375 | A1* | 7/2017 | Brosse ............... | C11D 17/0078 |

FOREIGN PATENT DOCUMENTS

| | | | | |
|---|---|---|---|---|
| EP | 2929870 | A1 | 10/2015 | |
| GB | 743222 | A | 1/1956 | |
| WO | WO-2019233937 | A1 * | 12/2019 | ............ B30B 15/32 |

OTHER PUBLICATIONS

Sivakumar R. Vaithiyalingam et al. "Critical factors in manufacturing multi-layer tablets-Assessing material attributes, in-process controls, manufacturing process and product performance" in International Journal of Pharmaceutics, 398, (2010) 9-13. (Year: 2010).*
International Preliminary Report on Patentability of PCT/IB2021/054502 issued Sep. 2, 2022.
Search Report and Written Opinion of PCT/IB2021/054502 issued on Oct. 11, 2021.

* cited by examiner

*Primary Examiner* — Blessing M Fubara
(74) *Attorney, Agent, or Firm* — Silvia Salvadori, P.C.; Silvia Salvadori

(57) ABSTRACT

A process is disclosed for the manufacture of a compressed product consisting of a multilayer tablet formed in a single compression operation.

4 Claims, 3 Drawing Sheets

PROCESS FOR MANUFACTURING A COMPRESSED PRODUCT

This application is a U.S. national stage of PCT/IB 2021/054502 filed on 25 May 2021, which claims priority to and the benefit of Italian Patent Application No. 102020000012685 filed on 28 May 2020, the contents of which are all incorporated herein by reference in their entireties.

The invention relates to a process for the manufacture of multilayer tablets by means of a single compression operation involving a number of layers having the same surface area or different surface areas.

PRIOR ART

U.S. Pat. No. 4,139,589 discloses a process for the manufacture of multilayer tablets that involves forming a number of individual layers by means of repeated separate compression stages, each with the material/ingredients constituting each single layer, followed by a final compression performed by applying a force greater than those applied in the previous compressions, so as to generate lasting cohesion of the various layers and the desired hardness and smoothness of the tablet surfaces.

Said process requires the various layers to have the same surface area.

Figure 1:
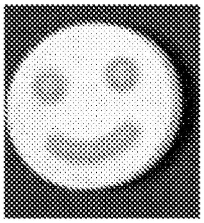

The technique described above could not be used to make a tablet characterised by layers having different surface areas or different shapes, as in the product illustrated in FIG. 1. In fact, if the individual layers to be compressed did not have the same surface area, the following undesirable consequences would result:

a) mixing of the ingredients of the various layers with consequent adverse effects on both the appearance and the formulation of the product, for example when the various layers contain different active ingredients which must not come into contact or be mixed with one another;

b) punch breakage.

EP 2 929 870 discloses multilayer tablets containing a chip, said tablets being obtained by compressing a particulate material both above and below said chip.

GB 743 222 discloses a tablet press for the production of coated tablets wherein the tablets are not removed from the mould during production. The device described does not allow the preparation of multilayer tablets with embossed parts.

DESCRIPTION OF THE INVENTION

A process for the preparation of a multilayer tablet characterised by layers having different surface areas has now been found. The process according to the invention which, unlike the known methods, involves a single final compression, comprises:

a) filling the upper surface of a punch (hereinafter also called "mould"), which slides inside the compression chamber of a tablet press, with a first particulate material;

b) raising the mould until the layer of material is conveyed to the upper extremity of the compression chamber;

c) removing the excess particulate material by scraping with a suitable device;

d) lowering the mould into the compression chamber and filling it with a second particulate material;

e) optionally repeating steps b), c) and d) for a number of times corresponding to the number of desired layers of the finished tablet;

f) compressing and ejecting the formed tablet.

Figure 2A:
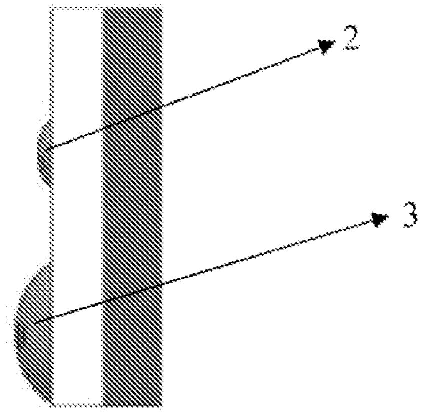
Figure 2B:
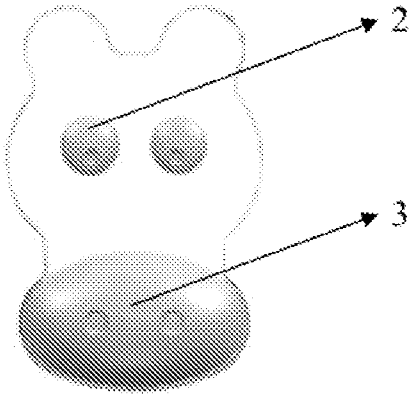

The mould can have any shape suitable for the formation of confectionery products, in particular multilayer candies. According to a preferred aspect of the invention, the mould has grooves/recesses that allow the creation of embossed layers so as to form figures and/or decorations on one of the layers of the tablet. An example of said embodiment is illustrated in FIGS. 2*a* and 2*b*, which represent a side view and front view respectively of a tablet wherein reference numbers 2 and 3 represent layers with different areas made with a specific mould having grooves/recesses.

Figure 3:
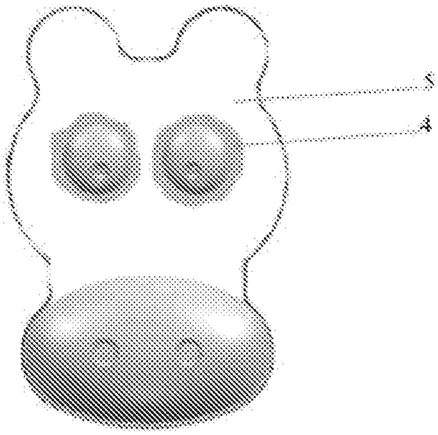
Figure 4:
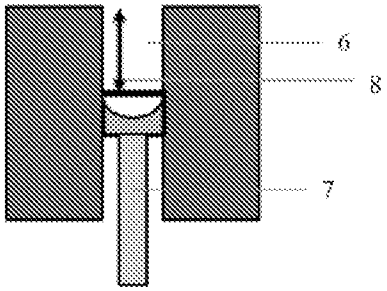
Figure 5:
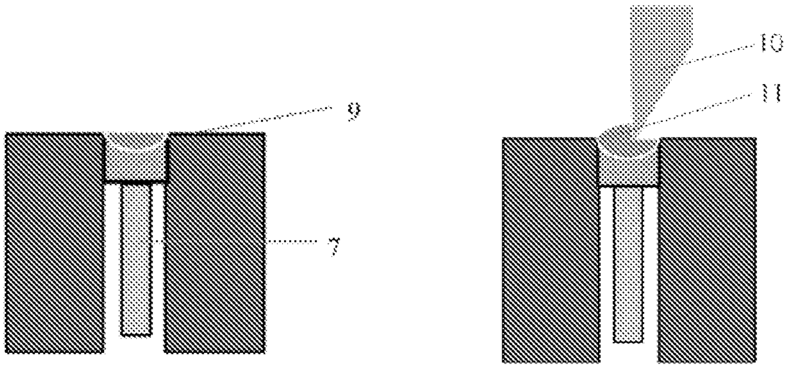
Figure 6:
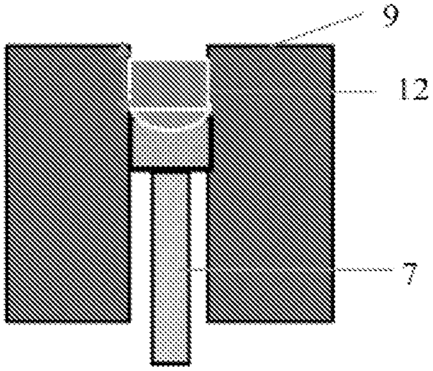
Figure 7:
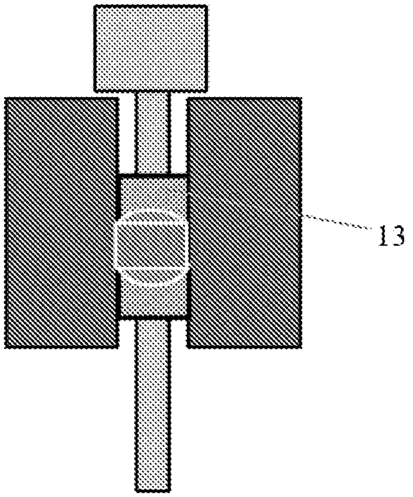

When operating according to the prior art, the grooves/recesses would have to be filled with an amount of material larger than that required to fill the recesses in order to allow the compression of layers 2 and 3 and prevent the mould and upper punch from coming into contact with one another, resulting in their breakage. However, after compression of said material, a surface portion of compressed material not retained in the recesses would form, leading to seepage 4 of the colour of the layers indicated above as 2 and 3 into the immediately adjacent layer 5, thus creating an unattractive appearance, as exemplified in FIG. 3.

Conversely, if it is desired to avoid the problem of mixing of the ingredients of the different layers when operating according to the prior art, a minimal amount of material would need to be used to prevent the seepage thereof at the time of compression. As stated above, however, using a minimal amount of material could cause breakage of the mould and upper punch, leading to machine stoppage.

The process of the invention, characterised by removal of excess particulate material after mould filling, eliminates said problems.

Excess particulate material can be removed with a tool such as a blade, spatula, brush or similar device, mounted on the tablet press and operated by mechanical, pneumatic or electromechanical means, according to conventional techniques.

The particulate material used in steps a) and d) can have the same or a different composition. Some examples of the most commonly used materials are sucrose, lactose, polyols such as xylitol, maltitol and sorbitol, isomalt, starch and colourings, together with conventional compression excipients (anti-caking agents, lubricants).

The process will now be described in detail by reference to FIGS. 4-7, showing a mould characterised by recesses that will form layers 2 and 3 illustrated in FIGS. 2*a* and 2*b*. Said mould (7 in FIG. 4) is placed in a compression chamber (6) and maintained at a given desired height (8).

The material intended for filling the recesses is introduced into the compression chamber in a pre-determined amount; this necessarily means that the material introduced does not exactly match the volume of the recesses, but it is in excess.

The mould (7) then rises to the height of level (9). At this point, scraper element or device (10) comes into operation, removing the excess material (11).

The mould (7) then falls from level (9) to a pre-determined height in the compression chamber. The space (12) thus created is then filled with the material required to form the next layer. The operation described above can be repeated as many times as the number of layers required to form the finished product.

When the desired number of layers has been reached, the upper punch (13) is lowered; said punch, which can also be characterised by any desired shape, compresses the material, thereby forming the end product.

Moreover, it is known that in the manufacture of a multilayer tablet, the weight ratio between each of the layers and the finished product must be not less than 25% (International Journal of Pharmaceutical Science & Research—Vol. 9—1 Mar. 2018—Multilayered Tablet: a novel approach for oral drug delivery—p. 878).

A number of technical tests demonstrate that when multilayer tablets wherein each layer has the same area are manufactured, a product according to the conventional system can be obtained until the weight ratio of the single layer to the total weight of the finished product does not fall below 10%.

Conversely, the present invention allows the production of multilayer tablets with layers having different surface areas, and in some cases even with layers having a minimal or much smaller area than the other layers, and having a weight ratio of the single layer to the total weight of the product which can even be below 2%.

As the process of the invention allows the manufacture of layers with different shapes and volumes, it is particularly suitable to allow the use of active ingredients (such as colourings, flavourings, plant extracts, whitening ingredients, Omega 3 fatty acids, breath fresheners, vitamins, minerals, etc.) in the formation of the tablet, and they can also be the only ingredients of a given layer without being mixed with another material having the sole purpose of allowing a minimum compressible volume to be reached.

In addition to the advantages listed above which relate to the manufacture of multilayer products having layers with different surface areas, the invention also solves various drawbacks in the manufacture of tablets having a plurality of layers with the same surface area, by maintaining the possibility of manufacturing them in a single compression operation.

The process of the invention prevents irregularities in the formation of the layers which, if differently coloured, would appear non-linear and therefore unattractive.

Figure 8:
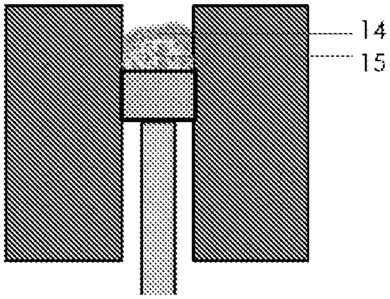

Said problem would arise if the excess particulate material were not removed because a levelled, linear, homogeneous distribution thereof would not be guaranteed when the compression chamber was filled with the material. In other words, the particulate material could be distributed in such a way as to form layers (14) and (15) as shown in FIG. 8.

The process of the invention also solves the problem of detachment of layers which can occur when excessively high compression is applied in an attempt to solve said problem of irregularities.

The invention is illustrated in greater detail in the following example.

Example 1

A mould characterised by the presence of grooves/recesses is used in a tablet press commonly used for tablet production in the pharmaceutical and food industries. Said mould and the recesses/grooves are designed to produce specific layers which may, if necessary, be small and/or of a particular shape, and in particular those layers that define the eyes and muzzle of a cow's head (FIG. 2).

Mould (7) falls into compression chamber (6) of the tablet press to the desired depth (8) of 0 mm, and the hollows are filled with 70 mg of a mixture of powdered sorbitol, aspartame, flavouring, magnesium stearate and blue colouring. At this stage only the mouth and eyes of the future cow are filled.

Mould (7) remains at the 0 mm level (9), and scraper device (10) is activated to remove the excess powder (11) on the upper part of the flat surface of the mould.

When the mould is subsequently filled, it falls back into compression chamber (6) of the tablet press to the desired depth (12) of 6 mm, and the compression chamber is filled with 630 mg of a mixture of powdered sorbitol, aspartame, flavouring and magnesium stearate.

Upper punch (13) falls into compression chamber (6), applying a pressure of 15 Pa to form the 700 mg tablet, wherein the cow's eyes and mouth are coloured and the rest of the tablet is white.

Upper punch (13) rises to the original position, mould (7) rises to floor level (9), and the tablet is ejected.

The invention claimed is:

1. A process for the preparation of a multilayer tablet which comprises:

a) filling the upper surface of a mould having recesses designed to form a tablet with layers not having the same surface area, said mould sliding in the compression chamber of a tablet press, with a first particulate material;

b) raising the mould until the layer of material is conveyed to the upper extremity of the compression chamber;

c) removing the excess particulate material by scraping with a scraper device;

d) lowering the mould into the compression chamber and filling with a second particulate material;

e) repeating steps b), c) and d) for a number of times corresponding to the number of desired layers of the finished tablet, the layers have different surface areas having a weight ratio of the single layer to the total weight of the product of less than 2%; and f) compressing and ejecting the formed tablet.

2. A process according to claim 1 wherein at least one layer has a weight ratio of less than 25% of the weight of the finished product.

3. A process according to claim 2 wherein the layers having different surface areas have a weight ratio of the single layer to the total weight of the product of less than 2%.

4. The process according to claim 1, wherein said desired layers formed in said step e) have different surface areas and different active ingredients.

* * * * *